United States Patent
Hoult et al.

(10) Patent No.: US 10,337,990 B2
(45) Date of Patent: Jul. 2, 2019

(54) IDENTIFYING PRESENCE OF SUBSTANCES

(71) Applicant: PerkinElmer Singapore PTE Limited, Singapore (SG)

(72) Inventors: Robert Alan Hoult, Buckinghamshire (GB); Ben Perston, Buckinghamshire (GB)

(73) Assignee: PERKINELMER SINGAPORE PTE LIMITED, Singapore (SG)

( * ) Notice: Subject to any disclaimer, the term of this patent is extended or adjusted under 35 U.S.C. 154(b) by 166 days.

(21) Appl. No.: 14/913,782

(22) PCT Filed: Jul. 25, 2014

(86) PCT No.: PCT/GB2014/000291
§ 371 (c)(1),
(2) Date: Feb. 23, 2016

(87) PCT Pub. No.: WO2015/025114
PCT Pub. Date: Feb. 26, 2015

(65) Prior Publication Data
US 2016/0209324 A1    Jul. 21, 2016

(30) Foreign Application Priority Data
Aug. 23, 2013  (GB) .................................. 1315195.6

(51) Int. Cl.
G01N 21/35  (2014.01)
G01N 33/04  (2006.01)
G01N 21/359 (2014.01)

(52) U.S. Cl.
CPC ........... *G01N 21/359* (2013.01); *G01N 21/35* (2013.01); *G01N 33/04* (2013.01); *G01N 2201/12* (2013.01); *G01N 2201/1293* (2013.01)

(58) Field of Classification Search
None
See application file for complete search history.

(56) References Cited

U.S. PATENT DOCUMENTS 5,781,284 A * 7/1998 Infante .................... G01N 21/85
356/432
6,748,334 B1 * 6/2004 Perez ................. G01N 21/3504
702/24

(Continued)

OTHER PUBLICATIONS

Labbe, N., "Extracting Information from Spectral Data", University of Tennessee, Forest Products Center, Jun. 10, 2007.*

(Continued)

*Primary Examiner* — J. E. Schoenholtz
(74) *Attorney, Agent, or Firm* — Nixon & Vanderhye PC

(57) ABSTRACT

A method for identifying the presence of at least one adulterant substance in a sample. The method comprises receiving sets of sample spectral data, reference spectral data, validation spectral data each set for a respective validation example, and adulterant substance spectral data for said at least one adulterant substance. From these residue data which is representative of a residue which would remain after performing a least squares fitting process between the sample spectral data and the reference spectral data is determined and modified sample residue data which is representative of a residue which would remain after performing a least squares fitting process between the sample spectral data, the reference spectral data and the adulterant substance spectral data is determined. The corresponding two residue data sets are also determined for each validation example. The method then includes performing at least one comparison amongst the sample residue data, the modified sample residue data, the validation residue data, and the modified validation residue data; and determining a likelihood value for the presence of said at least one adul- (Continued)

terant substance in said sample in dependence on said at least one comparison; and outputting said likelihood value.

26 Claims, 3 Drawing Sheets

(56) References Cited

U.S. PATENT DOCUMENTS

| | | | | |
|---|---|---|---|---|
| 8,296,106 | B2* | 10/2012 | Noll | G01J 3/28 |
| | | | | 250/339.07 |
| 2013/0193325 | A1* | 8/2013 | Phillips | G01N 21/3504 |
| | | | | 250/339.07 |
| 2013/0316467 | A1* | 11/2013 | Carron | G01N 33/54313 |
| | | | | 436/501 |
| 2015/0335248 | A1* | 11/2015 | Huang | G01N 21/65 |
| | | | | 600/476 |
| 2017/0160257 | A1* | 6/2017 | Shiley | G01N 33/24 |

OTHER PUBLICATIONS

O'Keefe, K. R., and H. V. Malmstadt. "Automated Computer-Controlled Spectrophotometer System for Kinetic or Equilibrium Methods of Analysis." Analytical Chemistry, vol. 47, No. 4, 1975, pp. 707-714., doi:10.1021/ac60354a037.*

Guinon, J. L., et al. "Interfacing an Old UV-VIS Spectrophotometer to a PC Computer." Journal of Chemical Education, vol. 72, No. 4, 1995, doi:10.1021/ed072pa81.*

Publishers summary of Spinelli, S., et al. "Chapter 11 UV Spectra Library." Techniques and Instrumentation in Analytical Chemistry UV-Visible Spectrophotometry of Water and Wastewater, 2007, pp. 267-356., doi:10.1016/s0167-9244(07)80013-8 downloaded from URLhttps://www.sciencedirect.com/science/article/pii/S0167924407800138 on Jul. 12, 2018.*

Beckman Instruments DU 800 UV/Visible Spectrophotometer, downloaded from URL <http://www.beckmancoulter.com/products/instrument/analytical/uvvis/du800_inst_dcr.asp> on Jun. 9, 2009.*

Wang et al., "Feasibility Study of Quantifying and Discriminating Soybean Oil Adulteration in Camellia Oils by Attenuated Total Reflectance MIR and Fiber Optic Diffuse Reflectance NIR", Food Chemistry, ElSelvier Ltd., NL, vol. 95, No. 3, Apr. 1, 2006, pp. 529-536.

Poliana M. Santos et al., "Application of Hand-Held and Portable Infrared Spectrometers in Bovine Milk Analysis", Journal of Agricultural and Food Chemistry, vol. 61, No. 6, Feb. 13, 2013, pp. 1205-1211.

Ben Perston et al., "Near Infrared Spectroscopy", Application Note, Nov. 20, 2013, pp. 1-6.

Meza-Marquez et al. "Application of Mid-Infrared Spectroscopy with Multivariate Analysis and Soft Independent Modeling of Class Analogies (SIMCA) for the Detection of Adulterants in Minced Beef", Meat Science, ElSelvier Science, GB, vol. 86, No. 2, Oct. 1, 2010, pp. 511-519.

International Preliminary Report on Patentability dated Mar. 3, 2016 in corresponding Application No. PCT/GB2014/000291.

* cited by examiner

IDENTIFYING PRESENCE OF SUBSTANCES

This application is the U.S. national phase of International Application No. PCT/GB2014/000291 filed 25 Jul. 2014 which designated the U.S. and claims priority to GB Patent Application No. 1315195.6 filed 23 Aug. 2013, the entire contents of each of which are hereby incorporated by reference.

This invention relates to the identification of the presence of substances. In particular it relates to the identification of at least one adulterant substance in a sample.

It is well known that in many instances a material can be identified from its spectrum, be it an optical spectrum, a mass spectrum, or other type of spectrum. It is often the case that the spectrum of a mixture of materials is a linear combination of the spectra of the individual materials, allowing the quantitative composition of the mixture to be determined by matching its spectrum to a linear combination of spectra of known materials. Mathematically this match is achieved by minimisation of the numerical differences between the material spectrum and trial combinations chosen from among the known spectra, selecting the best fit as representing the likely composition of the mixture.

The most commonly used measure of numerical difference in this type of work is the Euclidean norm and this process of matching is often known as a least-squares fit.

It is also well known that the spectra of nominally identical materials can differ slightly for a variety of reasons. The most fundamental reason is that samples of what is supposed to be identical material may actually differ slightly in composition or physical form but to this can be added systematic measurement differences—deviations from ideal performance in the measuring instrument such as baseline drift and resolution effects—as well as the inevitable random noise that accompanies all measurements.

The systematic differences between spectra of nominally the same material often have distinct spectral character. Consequently it may be that the different criteria can be substantially refined by considering the shape of any difference spectrum. A common way to achieve this is through principal component analysis (PCA). This well-known algorithm can examine the spectral differences (usually differences from the mean spectrum) to discover forms of correlated variation among the data that occur in more than one difference spectrum. The result is a series of spectral forms known as factors of descending significance that, in suitable combinations, describe the various spectral characters of the differences.

At the lower significance levels these factors blend into the random noise and it is expedient to consider only the most significant factors and lump the rest together under the heading of noise (the residue). Note that individual factors may not recognisably relate directly to main sources of differences because the factors are most likely combinations of such sources.

A particular issue today is being able to determine whether a material offered for sale is actually the material intended to be purchased or whether it is perhaps that material but with the addition of some adulterant. Adulterants in general are added to material in order to reduce the cost and increase the profability in its sale.

For a particular type of substance or sample there will typically be a number of known potential adulterants which could be used in this way without it being immediately obvious to the purchaser.

It may of course be possible to determine the inclusion of such adulterants in a product for purchase by time consuming and expensive wet chemical analysis techniques but what is desired is a quick and simple and preferably non-invasive/non-destructive analysis technique which may be used on samples to determine whether they are a "good" unadulterated material or one which has had adulterant substances added to it.

The present invention is aimed at addressing such a need.

One area where this is of particular interest is that of food stuffs. One can consider cheese as an example. It is possible that cheese may be adulterated by the addition of, say, non-milk protein to bulk out the cheese at a lower expense than the genuine ingredients. At the same time it will be appreciated that there can be significant variations in the content of cheese and thus any analysis technique needs to be able to alert the user to the likely presence of an adulterant substance in a sample whilst allowing normal variations which may be present in cheese to still be considered as cheese by the analysis method.

Another example may be a ground spice which could be potentially be bulked out by another finely ground material such as brick dust.

Whilst in principle the techniques discussed below might be used with spectral data of many different types as alluded to above, in the present case optical spectroscopy techniques are of particular interest and, for example, infrared spectroscopy is one particular technique that may be used in order to obtain the necessary spectra for use in the present techniques.

According to a first aspect of the present invention there is provided a method for identifying the presence of at least one adulterant substance in a sample comprising the steps of:

receiving a set of sample spectral data acquired for a sample, receiving a set of reference spectral data, receiving a plurality of sets of validation spectral data each set for a respective validation example, receiving a set of adulterant substance spectral data for said at least one adulterant substance;

determining sample residue data which is representative of a residue which would remain after performing a least squares fitting process between the sample spectral data and the reference spectral data;

determining modified sample residue data which is representative of a residue which would remain after performing a least squares fitting process between the sample spectral data, the reference spectral data and the adulterant substance spectral data;

for each validation example, determining validation residue data which is representative of a residue which would remain after performing a least squares fitting process between the validation spectral data for the respective example and the reference spectral data;

for each validation example, determining modified validation residue data which is representative of a residue which would remain after performing a least squares fitting process between the validation spectral data for the respective example, the reference spectral data and the adulterant substance spectral data;

performing at least one comparison amongst the sample residue data, the modified sample residue data, the validation residue data, and the modified validation residue data;

determining a likelihood value for the presence of said at least one adulterant substance in said sample in dependence on said at least one comparison; and outputting said likelihood value.

This allows the identification of the presence of an adulterant substance in a sample where there may be some considerable variation in the character of the sample, and its resulting spectral data, without this being indicative of the presence of an adulterant substance.

The reference spectral data is representative of a substance which is expected to be nominally the same as the sample if the sample does not contain adulterant substances.

The validation spectral data is different from the reference spectral data but still representative of a substance which is expected to be nominally the same as the sample if the sample does not contain adulterant substances.

One can consider there to be classes of substance. In such a case the reference spectral data and the validation spectral data can be chosen to be representative of substances in the same class as the sample.

An example of a class of substance might be cheese. Thus if the sample is cheese, the reference spectral data and the validation spectral data can be chosen to be representative of cheese. Depending on the circumstances the class might be chosen to be smaller. Thus if the sample is a particular type of cheese this might be the class and the reference spectral data and the validation spectral data can be chosen to be representative of that type of cheese.

The method can comprise the step of deciding on a class of substance to be used in dependence on the sample, and selecting the reference spectral data and the validation spectral data so as to be representative of substances in that class.

Each of the sample residue data, the modified sample residue data, the validation residue data, and the modified validation residue data may comprise a respective residual spectrum.

Each of the sample residue data, the modified sample residue data, the validation residue data, and the modified validation residue data may comprise a respective scalar value.

The scalar value may comprise the rms of a respective residual spectrum.

The step of performing at least one comparison may comprise,
a) determining a value of a metric in respect of:
i) the sample residue data;
ii) the modified sample residue data;
iii) the validation residue data for each validation example;
iv) the modified validation residue data for each validation example.

Values for more than one metric may be determined.

The rms of a respective residual spectrum may be chosen as a metric. This may be determined without first determining the spectrum itself as it is an intrinsic part/output of a least squares fitting process. Another possible metric trivially different from rms in this application is the standard deviation of the residual spectrum.

Other metrics will generally require determination of the residual spectrum as a first step.

Other possible metrics include:
a ratio of peak-peak amplitude to rms for the residual spectrum,
the number of runs in the residual spectrum, where a run is a contiguous stretch of data that all lies to the same side of zero,
the absolute area under each run,
the root mean square run length.

The step of performing at least one comparison may comprise,
a) determining a value of a metric in respect of:
i) the sample residue data;
ii) the modified sample residue data;
iii) the validation residue data for each validation example;
iv) the modified validation residue data for each validation example,
b) determining a maximum value of the metric for:
i) the validation residue data across the validation examples;
ii) the modified validation residue data across the validation examples,
c) determining an average value of the metric for:
i) the validation residue data across the validation examples;
ii) the modified validation residue data across the validation examples,
d) determining a standard deviation value of the metric for:
i) the validation residue data across the validation examples;
ii) the modified validation residue data across the validation examples, The step of performing at least one comparison may comprise,
a) determining a value of a metric in respect of:
i) the sample residue data;
ii) the modified sample residue data;
iii) the validation residue data for each validation example;
iv) the modified validation residue data for each validation example,
b) determining a maximum value of the metric for:
i) the validation residue data across the validation examples;
ii) the modified validation residue data across the validation examples, and
c) performing at least one comparison between the value of the metric for at least one of the sample residue data and the modified sample residue on the one hand and the determined maximum value of the metric for at least one of the validation residue data and the modified validation residue data on the other hand.

The step of performing at least one comparison may comprise,
a) determining a value of a metric in respect of:
i) the sample residue data;
ii) the modified sample residue data;
iii) the validation residue data for each validation example;
iv) the modified validation residue data for each validation example,
b) determining an average value of the metric for:
i) the validation residue data across the validation examples;
ii) the modified validation residue data across the validation examples,
c) determining a standard deviation value of the metric for:
i) the validation residue data across the validation examples;
ii) the modified validation residue data across the validation examples, and
d) performing at least one comparison between,
the value of the metric for at least one of the sample residue data and the modified sample residue on the one hand, and
one of:
i) the average for the validation residue data determined in b) plus a predetermined number (n) times the standard deviation for the validation residue data calculated in c); and
ii) the average for the modified validation residue data determined in b) plus a predetermined number (n) times the standard deviation for the modified validation residue data calculated in c)
on the other hand.

The step of performing at least one comparison may comprise,
a) determining a value of a metric in respect of:
i) the sample residue data;
ii) the modified sample residue data;
iii) the validation residue data for each validation example;

iv) the modified validation residue data for each validation example, b) calculating the difference between the value of the metric for the sample residue data and the value of the metric for the modified sample residue data, c) for each validation example, calculating the difference between the value of the metric for the validation residue data and the value of the metric for the modified validation residue data, d) determining an average difference between the value of the metric for the validation residue data and the value of the metric for the modified validation residue data across the validation examples, e) determining a standard deviation in the difference between the value of the metric for the validation residue data and the value of the metric for the modified validation residue data across the validation examples, f) comparing the difference between the value of the metric for the sample residue data and the value of metric for the modified sample residue data calculated in c) to the average determined in d) plus a predetermined number (n) times the standard deviation calculated in e).

The predetermined number (n) may be chosen to be 3.

This comparison illustrates the degree to which taking a possible adulterant spectra into account improves the fit to the sample, compared to the improvement seen for validation examples which should not contain the adulterant. If the improvement for the sample is smaller than the average for the validation examples this indicates that the adulterant is not present. If the improvement is significantly greater than the average this provides an indication that adulterant is present.

Preferably the step of performing at least one comparison comprises performing more than one comparison. Where values of metrics are calculated these may be used in a plurality of comparisons.

Where more than one comparison is performed the result of each comparison may be scored. The step of determining the likelihood value may include summing the scores.

The scoring may be as follows:
If the value of the metric for the sample exceeds the average of metric for the validation examples+n standard deviations, with n chosen to be equal to 3 or greater, score=2.
If the value of the metric for the sample exceeds the determined maximum metric for the validation examples, score=1.
Otherwise score=0.

The method may comprise the further step of estimating the concentration of a detected adulterant in the sample. This may be done on the basis of the size of a magnitude based fitting coefficient used in the fitting process.

The method may comprise the further step of determining a significance value for a change between the value of a metric in respect of the sample residue data and the modified sample residue data, the significance value being calculated as the difference between the value of a metric in respect of the sample residue data and the modified sample residue data divided by 6 times the determined standard deviation of the metric for the validation residue data across the validation examples.

The method may comprise the further step of outputting an indicator that the sample likely includes an adulterant which is distinct from said at least one adulterant when it is determined that i) the determined value of a metric in respect of the sample residue data is greater than the average for the validation residue data plus 3 times the standard deviation for the validation residue data; and ii) the determined value of a metric in respect of the modified sample residue data is greater than the average for the modified validation residue data determined in plus 3 times the standard deviation for the modified validation residue data.

The sample residue data may comprise the rms of a respective residual spectrum which would remain after performing a least squares fitting process between the sample spectral data and the reference spectral data.

The modified sample residue data may comprise the rms of a respective residual spectrum which would remain after performing a least squares fitting process between the sample spectral data, the reference spectral data and the adulterant substance spectral data.

The validation residue data may comprise the rms of a respective residual spectrum which would remain after performing a least squares fitting process between the respective validation spectral data and the reference spectral data.

The modified validation residue data may comprise the rms of a respective residual spectrum which would remain after performing a least squares fitting process between the respective validation spectral data, the reference spectral data and the adulterant substance spectral data.

The step of performing at least one comparison amongst the sample residue data, the modified sample residue data, the validation residue data, and the modified validation residue data may comprise comparing at least one respective pair of the rms values.

The method may comprise:
receiving a set of adulterant substance spectral data for a plurality of adulterant substances,
determining respective modified sample residue data which is representative of a residue which would remain after performing a least squares fitting process between the sample spectral data, the reference spectral data and each set of adulterant substance spectral data, and
for each validation example, determining respective modified validation residue data which is representative of a residue which would remain after performing a least squares fitting process between the validation spectral data for the respective example, the reference spectral data and each set of adulterant substance spectral data.

In such a case the step of performing at least one comparison may comprise
performing at least one comparison in respect of each adulterant substance; and
determining a likelihood value for the presence of each adulterant substance in said sample in dependence on said at least one comparison.

The method may comprise:
receiving a set of adulterant substance spectral data for a plurality of adulterant substance,
determining respective modified sample residue data which is representative of a residue which would remain after performing a least squares fitting process between the sample spectral data, the reference spectral data and at least one selected combination of sets of adulterant substance spectral data, and
for each validation example, determining respective modified validation residue data which is representative of a residue which would remain after performing a least squares fitting process between the validation spectral data for the respective example, the reference spectral data and the at least one selected combination of sets of adulterant substance spectral data.

In such a case the step of performing at least one comparison may comprise
performing at least one comparison in respect of each selected combination of adulterant substances; and
determining a likelihood value for the presence of each selected combination of adulterant substances in said sample in dependence on said at least one comparison.

At least one of the sets of validation spectral data may be based on a spectrum acquired using a spectrometer from a validation example substance.

This leads to validation residue data which is based on example substances.

Example substances with suitable characteristics and variability may be hard to come by and thus having an alternative method for determining validation data is useful.

Where the validation residue data comprises a residual spectrum, the method may comprise the step of creating an additional validation residue spectrum by the steps of:
computing a discrete wavelet transform of the validation residue spectrum for one validation example;
multiplying at least part of the transform point by point by a normally distributed sequence of random numbers with unit standard deviation to provide a modified transform;
performing an inverse of the discrete wavelet transform on the modified transform to produce a spectrum which is usable as an additional validation residue spectrum.

The process may be repeated, with different sequences of random numbers and/or different validation residue data, to produce further additional validation residue spectra.

The or each additional validation residue spectrum may be used to determine additional validation residue data. This data can be used as, or in the same way as, validation residue data in the processes described above. The additional validation residue data is representative of a residue which would remain after performing a least squares fitting process between a respective randomised validation spectrum and the reference spectral data.

In an alternative the process used to create an additional validation residue spectrum may be used to create additional validation spectral data by operating on an initial set of validation spectral data rather than a residual spectrum. In such a case an additional validation residue spectrum can then be created by further operating on the additional set of validation spectral data.

The method may comprise the step of determining modified additional validation residue data which is representative of a residue which would remain after performing a least squares fitting process between the respective randomised validation spectrum, the reference spectral data and the adulterant substance spectral data.

The step of performing at least one comparison, may comprise performing at least one comparison amongst the sample residue data, the modified sample residue data, the validation residue data, the modified validation residue data, the additional validation residue data, and the modified additional validation residue data.

Metrics for the additional validation residue data, and the modified additional validation residue data may be determined as described above, and may be used as described above, in respect of the validation and modified validation residue data.

Where the expression "the validation residue data for each example" is used above this can comprise the additional validation residue data.

Where the expression "the modified validation residue data for each example" is used above this can comprise the additional modified validation residue data.

It can be useful to compare any improvement seen in taking adulterant substances into account against a random result. To facilitate this the method may comprise generating at least one randomly altered sample residue spectrum.

Where the sample residue data comprises a residual spectrum, the method may comprise the step of generating at least one randomly altered sample residue spectrum by steps of:
computing a discrete wavelet transform of the sample residue data;
multiplying at least part of the transform point by point by a normally distributed sequence of random numbers with unit standard deviation to provide a modified transform;
performing an inverse of the discrete wavelet transform operation on the modified transform to produce a spectrum which is usable as a randomly altered sample residue spectrum.

The process may be repeated, with different sequences of random numbers, to produce further randomly altered sample residue spectra.

The or each randomly altered sample residue spectrum may be used to determine randomly altered sample residue data. This can be used as, or in the same way as, validation residue data in the processes described above. The randomly altered sample residue data is representative of a residue which would remain after performing a least squares fitting process between a respective randomised spectrum and the reference spectral data.

Further the method may comprise the step of determining modified randomly altered sample residue data which is representative of a residue which would remain after performing a least squares fitting process between the respective randomised spectrum, the reference spectral data and the adulterant substance spectral data.

The step of performing at least one comparison, may comprise performing at least one comparison amongst the sample residue data, the modified sample residue data, the validation residue data, the modified validation residue data, randomly altered sample residue data, and modified randomly altered sample residue data, and also where present, the additional validation residue data, and the modified additional validation residue data.

Metrics for the randomly altered sample residue data and the modified randomly altered sample residue data may be determined as described above, and may be used as described above, in respect of the validation and modified validation residue data.

The randomly altered sample residue data and modified randomly altered sample residue data can be considered to be a special type of validation residue data.

The step of performing at least one comparison may comprise,
a) determining a value of a metric in respect of:
i) the sample residue data;
ii) the modified sample residue data;
iii) the randomly altered sample residue data for each randomised spectrum;
iv) the modified randomly altered sample residue data for each randomised spectrum;
and optionally
v) the validation residue data for each validation example;
vi) the modified validation residue data for each validation example.

The step of performing at least one comparison may comprise
a) for each randomised spectrum, calculating the difference between the value of the metric for the randomly altered sample residue data and the value of the metric for the modified randomly altered sample residue data, and at least one of
b) determining an average difference between the value of the metric for the randomly altered sample residue data and the value of the metric for the modified randomly altered sample residue data across the data set,
c) determining a standard deviation in the difference between the value of the metric for the randomly altered sample residue data and the value of the metric for the modified randomly altered sample residue data across the data set,
d) determining a maximum difference between the value of the metric for the randomly altered sample residue data and the value of the metric for the modified randomly altered sample residue data across the data set.

The step of performing at least one comparison may comprise,
a) determining a value of a metric in respect of:
i) the sample residue data;
ii) the modified sample residue data;
iii) the randomly altered sample residue data for each randomised spectrum;
iv) the modified randomly altered sample residue data for each randomised spectrum;
b) calculating the difference between the value of the metric for the sample residue data and the value of metric for the modified sample residue data,
c) for each randomised spectrum, calculating the difference between the value of the metric for the randomly altered sample residue data and the value of the metric for the modified randomly altered sample residue data,
d) determining an average difference between the value of the metric for the randomly altered sample residue data and the value of the metric for the modified randomly altered sample residue data across the data set,
e) determining a standard deviation in the difference between the value of the metric for the randomly altered sample residue data and the value of the metric for the modified randomly altered sample residue data across the data set,
f) comparing the difference between the value of the metric for the sample residue data and the value of metric for the modified sample residue data calculated in c) to the average determined in d) plus a predetermined number (n) times the standard deviation calculated in e).

The step of performing at least one comparison may comprise,
a) determining a value of a metric in respect of:
i) the sample residue data;
ii) the modified sample residue data;
iii) the randomly altered sample residue data for each randomised spectrum;
iv) the modified randomly altered sample residue data for each randomised spectrum;
b) calculating the difference between the value of the metric for the sample residue data and the value of metric for the modified sample residue data,
c) for each randomised spectrum, calculating the difference between the value of the metric for the randomly altered sample residue data and the value of the metric for the modified randomly altered sample residue data,
d) determining a maximum difference between the value of the metric for the randomly altered sample residue data and the value of the metric for the modified randomly altered sample residue data across the data set,
e) comparing the difference between the value of the metric for the sample residue data and the value of metric for the modified sample residue data calculated in c) to the maximum difference determined in d).

The steps of determining sample residue data, determining modified sample residue data, determining validation residue data, determining modified validation residue data may be carried out by directly performing the respective least squares fitting processes.

However this is computationally very intensive. Thus a different approach is preferred.

Thus the method may comprise the steps of:
developing a principal components analysis model of a calibration set of data to produce a set of principal factors which represent the set of reference spectral data;
projecting the principal factors out of the sample spectral data to leave the sample residue data;
projecting the principal factors out of the validation spectral data each set for a respective validation example to leave the validation residue data;
projecting the principal factors out of the adulterant substance spectral data for said at least one adulterant substance to leave adulterant residue data;
least squares fitting the sample residue data with the adulterant residue data to generate the modified sample residue data;
least squares fitting the validation residue data with the adulterant residue data to generate the modified validation residue data.

Where there are a plurality of sets of spectral data for different adulterant substances, combinations of the adulterant residue data for the respective substances may be used in the least squares fitting processes to generate the appropriate modified sample residue data and modified validation residue data.

The method may comprise the step of pre-processing the sample spectral data, the reference spectral data and the validation spectral data before the steps of determining the residue data.

Where the method includes developing a principal components analysis model of a calibration set of data, the calibration set of data may be pre-processed before the step of developing a principal components analysis model.

The pre-processing may comprise any one or any combination of:
ensuring that the spectra have the same start and end wavenumber/wavelength and the same data interval,
digital filtering,
weighting,
baseline suppression,
projecting out of unwanted effects.

The step of projecting out unwanted effects may comprise producing an orthonormal set of factor spectra from spectra of the unwanted effects and subtracting out a scaled amount of each factor from the spectral data for the sample, the validation examples and the adulterant substances.

The unwanted effects may include one or more of baseline effects, an average spectrum calculated from the spectra of the validation examples.

The spectral data used in the method may be acquired using one of a number of different forms of spectral analysis. Infrared spectroscopy, for example, near infrared spectroscopy and particular near infrared diffuse reflectance spectroscopy is one form of spectral analysis which is particularly suitable.

According to a second aspect of the present invention there is provided a method for identifying the presence of at least one adulterant substance in a sample comprising the steps of:
receiving a set of sample spectral data acquired for a sample,
receiving a plurality of sets of calibration spectral data for use in generating a set of reference spectral data, each set of calibration spectral data being for a respective calibration example,
receiving a plurality of sets of validation spectral data, each set for a respective validation example,
receiving a set of adulterant substance spectral data for said at least one adulterant substance;
developing a principal components analysis model of the calibration sets of data to produce a set of principal factors which represent the set of reference spectral data;
projecting the principal factors out of the sample spectral data to leave sample residue data;
projecting the principal factors out of each set of validation spectral data to leave validation residue data for each validation example;
projecting the principal factors out of the adulterant substance spectral data for said at least one adulterant substance to leave adulterant residue data;
least squares fitting the sample residue data with the adulterant residue data to generate modified sample residue data, which represents an effect of taking the adulterant spectral data into account in the principal components analysis model;
least squares fitting the validation residue data with the adulterant residue data to generate the modified validation residue data, which represents an effect of taking the adulterant spectral data into account in the principal components analysis model,
performing at least one comparison amongst the sample residue data, the modified sample residue data, the validation residue data, and the modified validation residue data;
determining a likelihood value for the presence of said at least one adulterant substance in said sample in dependence on said at least one comparison; and outputting said likelihood value.

According to a third aspect of the present invention there is provided a spectrometer including an analysis module arranged for identifying the presence of at least one adulterant substance in a sample using a method as defined above.

According to a fourth aspect of the present invention there is provided a spectrometer arranged for identifying the presence of at least one adulterant substance in a sample, the spectrometer having means arranged to:
acquire a set of sample spectral data for a sample,
determine or receive a set of reference spectral data,
acquire or receive a plurality of sets of validation spectral data each set for a respective validation example,
acquire or receive a set of adulterant substance spectral data for said at least one adulterant substance;
determine sample residue data which is representative of a residue which would remain after performing a least squares fitting process between the sample spectral data and the reference spectral data;
determine modified sample residue data which is representative of a residue which would remain after performing a least squares fitting process between the sample spectral data, the reference spectral data and the adulterant substance spectral data;
for each validation example, determine validation residue data which is representative of a residue which would remain after performing a least squares fitting process between the validation spectral data for the respective example and the reference spectral data;
for each validation example, determine modified validation residue data which is representative of a residue which would remain after performing a least squares fitting process between the validation spectral data for the respective example, the reference spectral data and the adulterant substance spectral data;
perform at least one comparison amongst the sample residue data, the modified sample residue data, the validation residue data, and the modified validation residue data;
determine a likelihood value for the presence of said at least one adulterant substance in said sample in dependence on said at least one comparison; and output said likelihood value.

According to a fifth aspect of the present invention there is provided a computer arranged under the control of software for processing spectral data to identify the presence of at least one adulterant substance in a sample,
the computer arranged to:
receive a set of sample spectral data for a sample,
determine or receive a set of reference spectral data,
receive a plurality of sets of validation spectral data each set for a respective validation example,
receive a set of adulterant substance spectral data for said at least one adulterant substance;
determine sample residue data which is representative of a residue which would remain after performing a least squares fitting process between the sample spectral data and the reference spectral data;
determine modified sample residue data which is representative of a residue which would remain after performing a least squares fitting process between the sample spectral data, the reference spectral data and the adulterant substance spectral data;
for each validation example, determine validation residue data which is representative of a residue which would remain after performing a least squares fitting process between the validation spectral data for the respective example and the reference spectral data;
for each validation example, determine modified validation residue data which is representative of a residue which would remain after performing a least squares fitting process between the validation spectral data for the respective example, the reference spectral data and the adulterant substance spectral data;
perform at least one comparison amongst the sample residue data, the modified sample residue data, the validation residue data, and the modified validation residue data;
determine a likelihood value for the presence of said at least one adulterant substance in said sample in dependence on said at least one comparison; and output said likelihood value.

According to a sixth aspect of the present invention there is provided a computer arranged under the control of software for processing spectral data in accordance with any method as defined above to identify the presence of at least one adulterant substance in a sample.

According to a seventh aspect of the present invention there is provided a computer program comprising code portions which when loaded and run a computer cause the computer to carry out the steps of:
receiving a set of sample spectral data for a sample,
determining or receiving a set of reference spectral data,
receiving a plurality of sets of validation spectral data each set for a respective validation example,
receiving a set of adulterant substance spectral data for said at least one adulterant substance;
determining sample residue data which is representative of a residue which would remain after performing a least squares fitting process between the sample spectral data and the reference spectral data;
determining modified sample residue data which is representative of a residue which would remain after performing a least squares fitting process between the sample spectral data, the reference spectral data and the adulterant substance spectral data;
for each validation example, determining validation residue data which is representative of a residue which would remain after performing a least squares fitting process between the validation spectral data for the respective example and the reference spectral data;
for each validation example, determining modified validation residue data which is representative of a residue which would remain after performing a least squares fitting process between the validation spectral data for the respective example, the reference spectral data and the adulterant substance spectral data;
performing at least one comparison amongst the sample residue data, the modified sample residue data, the validation residue data, and the modified validation residue data;
determining a likelihood value for the presence of said at least one adulterant substance in said sample in dependence on said at least one comparison; and outputting said likelihood value.

According to an eighth aspect of the present invention there is provided a computer program comprising code portions which when loaded and run on a computer cause the computer to carry out the steps of any of the methods defined above.

There may be a computer program product comprising a machine readable data carrier carrying the program of the seventh or eighth aspects of the invention.

Note that the subfeatures explained above following the first aspect of the invention are equally relevant as subfeatures of the remaining aspects of the invention and could be re-written in full with any necessary changes in wording, this is only not done in the interests of brevity.

Each method defined above may comprise a method of using (preferably optical) spectroscopy data to identify the presence of at least one adulterant substance in a sample.

Each method defined above may comprise a method of processing (preferably optical) spectroscopy data to provide an indication of the likelihood of the presence of at least one adulterant substance in a sample.

According to a ninth aspect of the invention there is provided a method for generating a randomised spectrum from an initial spectrum for use in spectral analysis, the method comprising steps of:
computing a discrete wavelet transform of the initial spectrum;
multiplying at least part of the transform point by point by a normally distributed sequence of random numbers with unit standard deviation to provide a modified transform;
performing an inverse of the discrete wavelet transform operation on the modified transform to produce a spectrum which is usable as a randomly altered spectrum.

The process may be repeated, with different sequences of random numbers, to produce further randomly altered spectra.

The initial spectrum may be a residue spectrum. The initial spectrum may be a sample spectrum. The initial spectrum may be a validation spectrum.

Such spectra may be useful where limited initial spectra are available and/or where it is desired to investigate the effect of random variations in spectra which might be expected to occur due to physical effects and variations. More realistic results should be achieved than directly randomising the original spectrum.

Embodiments of the present invention will now be described, by way of example only, with reference to the accompanying drawings, in which.

The present apparatus and techniques are arranged for identifying the presence of at least one adulterant substance in a sample. The apparatus and techniques make use of analysing the spectral data from the sample, together with spectral data from other substances, which are nominally the same as the sample, assuming that it is unadulterated, and also the spectra for known adulterants.

The sample spectra clearly have to be acquired for each sample as and when it is to be analysed.

On the other hand, the remaining spectral data may be acquired, at least partly, in a one time or periodic collection operation, or alternatively may be acquired each time analysis of samples is to take place.

As mentioned in the introduction, the present techniques may be used for identifying the presence of at least one adulterant substance with different types of spectroscopic analysis. Thus, for example, the initial spectral data may be acquired using an optical spectroscopy technique or a mass spectroscopy technique, or any other suitable spectroscopy technique, where the resulting spectrum will be indicative of a particular substance.

At the present time optical spectroscopy based techniques are of particular interest. Infrared spectroscopy being one of those and diffuse reflectance near infrared spectroscopy being of particular interest due to its appropriateness for use in identifying adulterant substances which may be present in foodstuffs samples which is a current area of particular interest.

Thus the remainder of this description will be written in terms of a system and technique relying on use of infrared spectroscopy, but it will be appreciated that the present techniques are not at all limited to the use of this type of spectroscopy. Furthermore much of the description below will in fact be generic to any and all types of spectroscopy which might be used for acquiring the spectral data.

Figure 1:
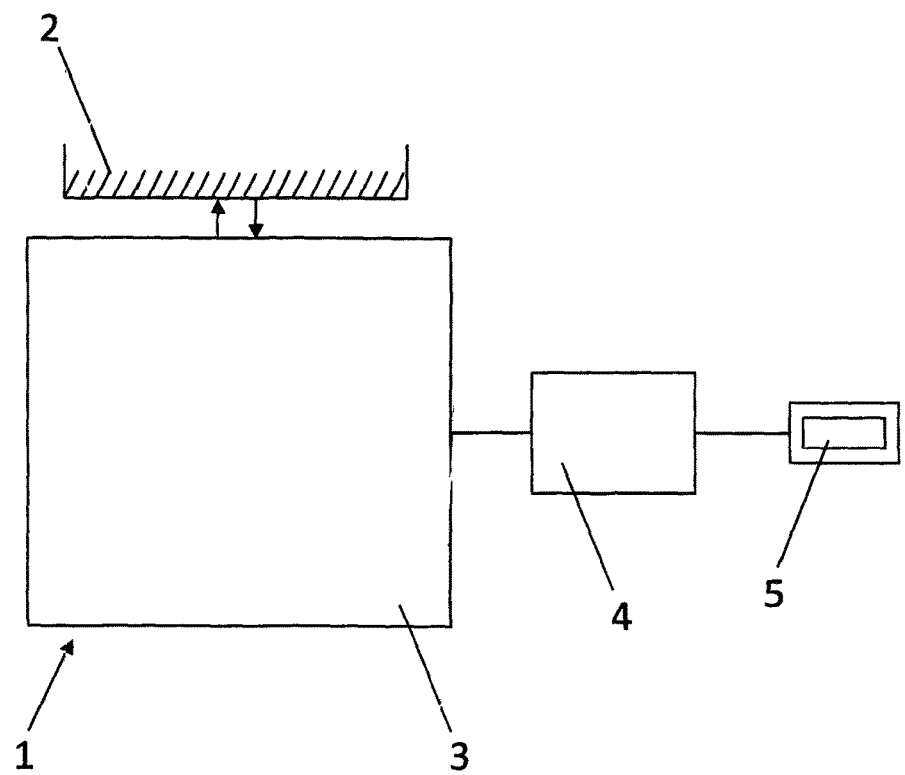
FIG. 1 is a schematic view of a spectrometer arranged for identifying the presence of at least one adulterant substance in a sample.

FIG. 1 schematically shows a spectrometer 1 for obtaining spectra from samples 2. The spectrometer 1 comprises a main body portion 3, an analysis module 4, and an output device 5.

It will be appreciated that in some circumstances an analysis module 4 and/or output device 5 such as a screen or printer may be provided separately from the spectrometer.

The analysis module 4 typically will comprise a computer which can be used in the analysis and determining steps which form part of the present techniques which will be described in more detail below. When suitably programmed, such a computer can embody the present invention. Similarly when the analysis module of the spectrometer is suitably programmed this may also embody the present invention.

The invention may also be embodied in a computer program which may be carried on a physical data carrier such as a CD, DVD, hard drive, flash drive or similar machine readable data carrier.

Figure 2:
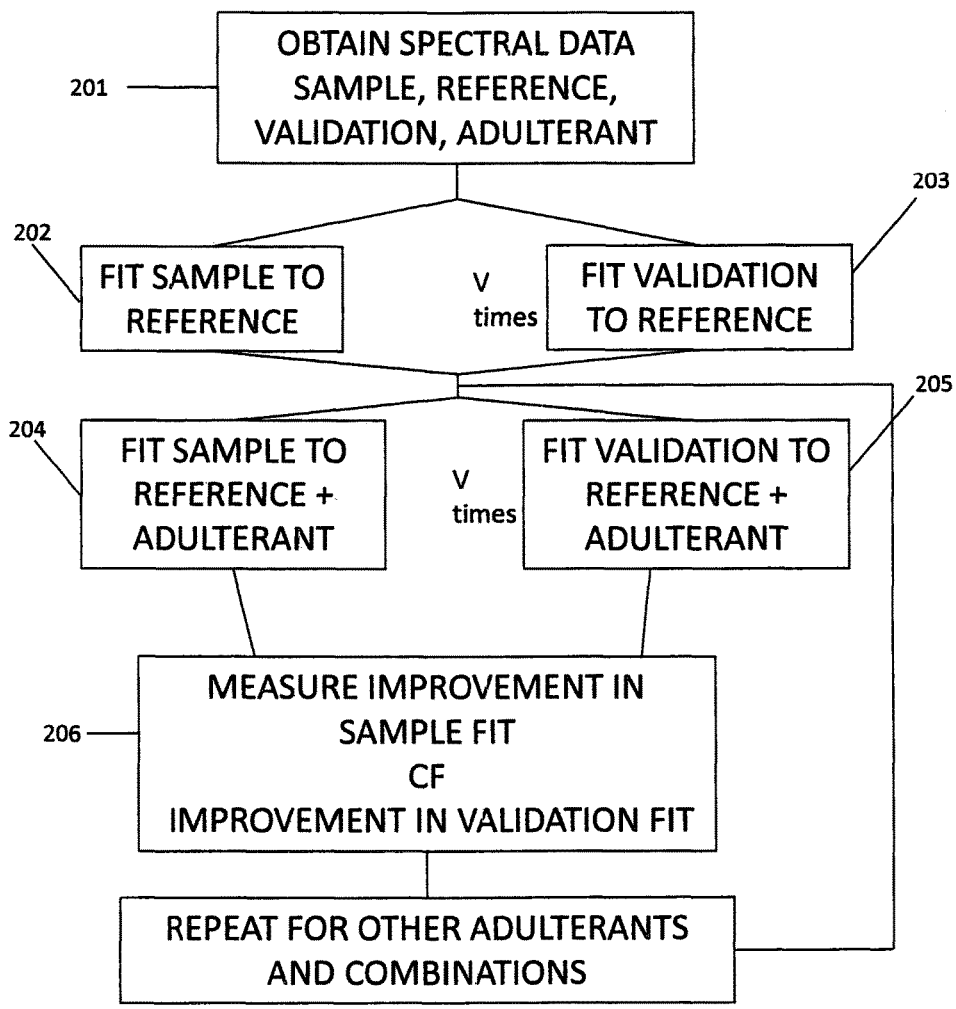
FIG. 2 is a flow chart showing, in highly schematic form, the principles underlying the present techniques.

FIG. 2 shows in highly schematic form the basic overall process which is performed when carrying out the present techniques in embodiments of the present invention.

In step 201 spectral data is obtained for a sample, a reference spectrum, a set of validation examples and a plurality of adulterant substances. In each case this spectral data may at least start with at least one spectrum being acquired using the spectrometer 1. Of course, in each case, the spectral data obtained for the sample, reference material, validation examples and adulterants will be representative of the respective substances.

In step 202 a fit is carried out between the sample spectral data and the reference spectral data, whereas in step 203 a fit is carried out between each set of validation spectral data and the reference spectral data. Thus step 203 is carried out v times where there are v different validation examples.

In step 204 a fit is carried out between the sample on the one hand and the reference spectral data and adulterant spectral data on the other hand. Thus the idea here is to see whether if the spectrum for particular adulterant is taken into account, this leads to a better fit. To put this another way, the question being asked is whether that particular adulterant is in fact present in the sample.

In step 205 a fit is carried out between the validation spectral data for particular validation example on the one hand, and the reference spectral data and the adulterant spectral data on the other hand. Again this process is carried out v times where there are v validation examples.

In step 206 comparisons can be made between the results of the fits carried out in each of steps 202 to 205. In particular, it is possible to measure whether the improvement in fit to the sample in step 204 made by including consideration of the adulterant is greater than/significant in the context of the improvement which is seen when the validation spectral data is fitted to the reference spectral data and the corresponding adulterant spectral data. As will be appreciated, this acts as a check on whether any improvement seen in fit to the sample when taking this particular adulterant into account is real or just a trivial/chance improvement. This comparison process will be defined in more detail further below.

After this comparison process has been carried in respect of a particular adulterant, steps 204 and 205 may be repeated for other adulterant substances and indeed combinations of adulterant substances.

In theory there is no limit to the number of different adulterants and adulterant combinations which may be considered in a process such as this. However it will be appreciated that there can be practical considerations to take into account in terms of the amount of data processing which is to be carried out. Thus it may, for example, be practical to consider combinations of up to three adulterants as being present in any one sample and thus carry out steps 204 and 205 in respect of fitting the sample and validation data to the reference plus up to three different adulterant substances.

The sample spectral data is self-evidently the spectral data which relates to the sample. On the other hand the reference spectral data is spectral data representing a good or clean substance of the same type as the sample. The reference spectral data may in fact be obtained by processing spectra from a number of example substances which are of the nominally same type as the samples to be tested.

Similarly the validation spectral data each relate to spectral data taken from a substance which is nominally the same as the sample.

To give a specific example, if the current techniques are to be used in the situation where the sample is cheese, then the reference spectral data will be that corresponding to at least one example of unadulterated cheese and the validation sets of spectral data will each relate to other unadulterated samples of cheese.

On the other hand, of course, the adulterant spectral data will relate to substances which are known for use as adulterants added to cheese.

It will be appreciated that the present techniques may be used in relation to many different substances or classes of substances. In each case it will be important to obtain reference spectral data and validation spectral data in relation to "good" or "clean" examples of substances which are nominally the same or in the same class as that of the sample which is to be investigated and similarly to obtain adulterant spectral data which it is known or suspected may be used to adulterate the type of substance of which the sample is an example.

It should be noted that the process described in FIG. 2 is a generalised conceptual process which underlies the present techniques. The actual implementation of the present techniques might follow the same steps shown in FIG. 2 but this is not necessarily the case.

In particular, in the currently preferred implementation of the present techniques, a slightly different series of steps is undertaken which have the same conceptual result as the steps shown in FIG. 2 but the actual processing steps carried out are different.

Figure 3:
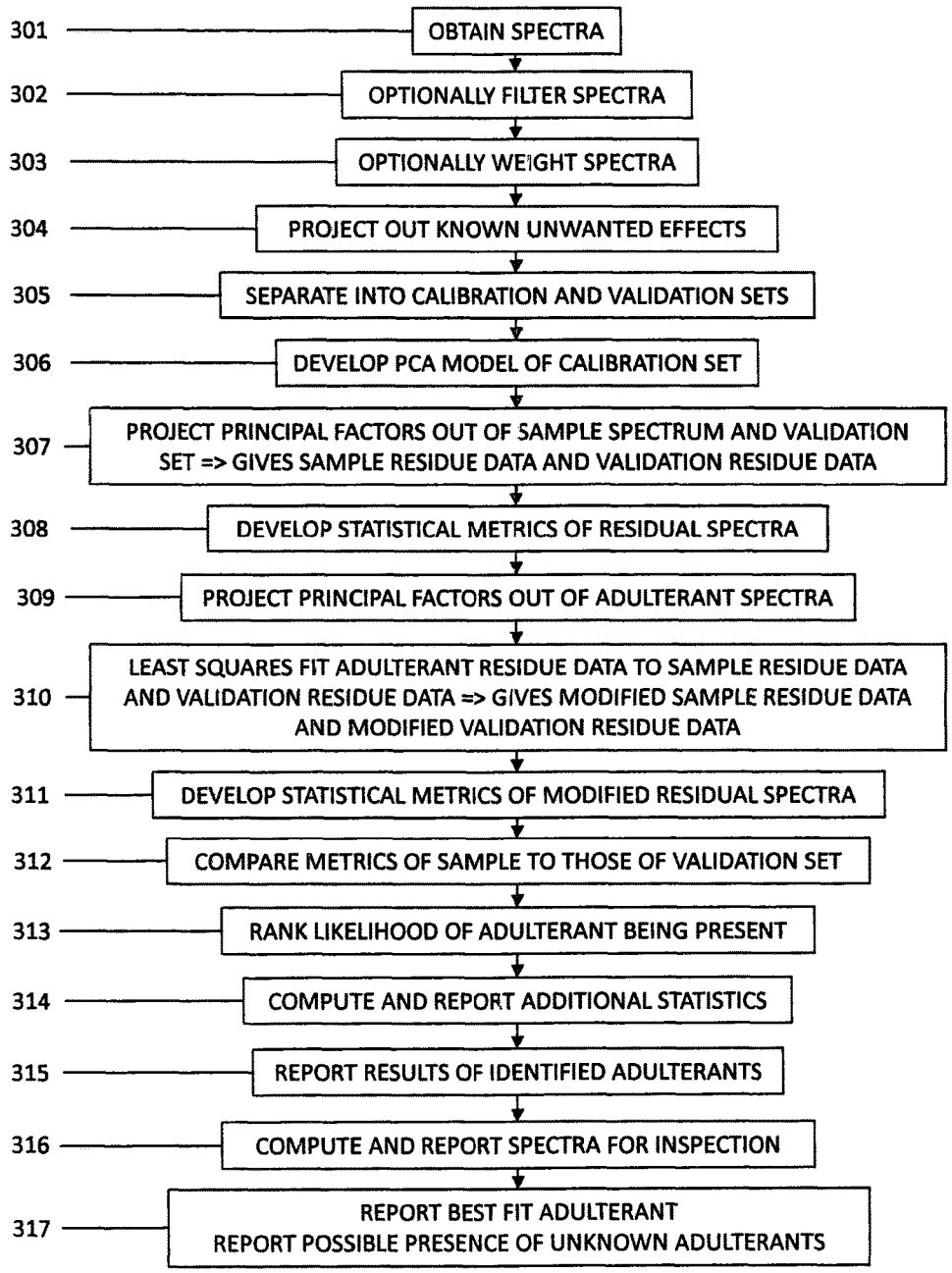
FIG. 3 is a flow chart showing the steps carried out in one particular implementation of the present techniques.

FIG. 3 is a flow chart showing a series of steps which are taken in particular implementation of the present techniques.

In step 301 spectra are obtained. As mentioned above these may all be obtained by the spectrometer 1 which will be used for analysing the sample under test or some of them may be obtained separately/earlier. An important part of this first step 301 is to gather consistent digital spectra. Preferably they are measured under very similar conditions. The spectra gathered comprise:
a) spectrum of sample under test
b) comparison spectra of known unadulterated material—such spectra should be representative of all expected sample variation
c) spectra of possible adulterants
d) spectra of known unwanted effects (e.g. baseline and water vapour absorption)—typical baselines can be simulated by polynomial curves.

Note that all spectra need to be compatible. That is they should have the same start and end wavenumber/wavelength and the same data interval. Spectra may be shortened/interpolated through a common range to achieve this or indeed to restrict the range of spectrum considered by the current processes. As far as practical, spectra should be measured under the same conditions to avoid introducing unnecessary inconsistencies. Spectra are assumed to be additive for the purposes of mixture analysis; logarithmic, or other conversion may be required to achieve this.

All of the spectra may be pre-processed in the same way according to choices made by the user.

Thus in step 302 the spectra may optionally be filtered. Note that the same digital filter should be used on all spectra.

Possible filtering includes smoothing (low pass filter) to reduce high resolution noise, differentiation (high pass filter) to reduce baseline effects, or a combination (band pass filter) might be the best choice. Further, notch filtering can be used to reduce periodic noise (e.g. fringes). Fourier transform filters can be used to tailor response. Discrete wavelet filters can be used to reduce known problem areas.

As a further form of pre-processing the spectra may all be weighted in step 303. Again all spectra should be treated the same, such that if there is any weighting, all spectra should be multiplied by the same weighting spectrum. Weighting can be graded according to the expected reliability of the spectral region. Low signal to noise regions will be given low weighting. Low weighting would also be given to regions of irrelevant variability (e.g. water vapour absorption). Signal to noise ratio could be estimated from replicate spectra or general considerations of spectral energy throughput. In the current implementation, weight is never allowed to go to zero but can be truncated at a very low value. This allows the unweighted spectrum to be reconstructed by dividing by the weight spectrum if and when desired.

Following any such optional filtering in step 302 and/or weighting in step 303, in step 304 known unwanted effects are projected out of the data spectra. That is to say out of each of the spectra listed at a) to c) above in the description of step 301. The step of projecting out known unwanted effects in the present implementation comprises using singular value decomposition or similar to produce an orthonormal set of factor spectra from the pre-processed spectra (d)) of unwanted effects. Then a scaled amount of each factor is subtracted away from all of the remaining spectra i.e. the spectra labelled a) to c) above. The scale is given by the scalar product of the spectrum being processed and the respective factor.

Note that it may be advantageous to include the mean of the comparison spectra (b) in the list above) as an unwanted effect and to subtract this from all of the data spectra a) to c). This can help later numerical stability as it means that later processing is carried out only in respect of differences in the spectra rather than the whole value.

Note that this process of projecting out is equivalent to least-squares fitting of the group of unwanted spectra to the remaining spectra and subtracting away the fit. It would also be possible to defer the process and instead include the unwanted spectra in the calibration set model which will be explained in more detail below.

In step 305 the comparison spectra (b) mentioned in relation to step 301) are separated into calibration and validation sets. This separation is somewhat arbitrary as each of the comparison spectra are chosen to be representative of unadulterated substances which are nominally the same as the samples which are to be considered in due course. A number of such examples are needed in the present techniques to act as a calibration set to allow the generation of the reference spectral data. Further a number are required as validation examples to check whether any improvement in fit when taking adulterants into account, is a real effect as discussed in general terms above. The selection of the calibration and validation sets from the comparison spectra might be carried out by the user or selected randomly by the system. Random selection by the system is preferred since it will avoid any effects that might be introduced by user choice.

In step 306 a Principal Components Analysis (PCA) model of the calibration set is developed. Production of the PCA model may be accomplished using singular value decomposition (SVD) or non-linear iterative partial least-squares (NIPALS) algorithms. The number of factors to be used in the model can be determine by checking either the singular values (eigenvalues) or the model residues. There are various well established tests such as Malinowski's indicator function or the F test that can be used. The number of factors can also be determined from the residues in the validation set as the factors are progressively projected out. For low numbers of calibration spectra all of the factors may be needed. In this case the method becomes equivalent to least-square fitting. Least-square fitting can still be used when this is not the case but it is expected that the process will become noisier.

Once the principal factors of the PCA model are known these may be used to process the sample spectrum and validation set. Thus in step 307 the principal factors are projected out of the sample spectrum and each of the validation set spectra. What remains in each case is the residual spectrum from fitting the calibration model in combination with the spectra of unwanted effects=the sample residue data and the validation residue data.

At this stage the residual spectra from the sample and for each example in the validation set may be considered.

In step 308 statistical metrics of the residual spectra are developed which may be used in a comparison process later. When deciding what metrics to use it is important to bear in mind that initially it is of interest whether the sample spectrum is abnormal i.e. likely to result from the sample including an adulterant material. To some degree this can be achieved by comparing the residual spectrum of the sample with the residuals of the validation spectra.

For any metric applied to the validation residual data, because there are multiple validation examples and therefore multiple validation residual spectra/data, it is possible to calculate an average for the metric and its standard deviation. A good rule of thumb is that if the metric for the sample spectrum lies outside the range of average+/−3 standard deviations (of the validation data) the sample spectrum is abnormal. The value of +/−3 standard deviations is a first choice but somewhat arbitrary. In some circumstances therefore a larger number of standard deviations might be chosen as a measure. This could be particularly relevant where there are a limited number of validation examples.

The root mean square value (rms) for each residual spectrum is easily calculated and serves as a summary statistical metric. Note that this metric can be computed without actually computing the residual spectrum since it is an intrinsic part of the least-squares process. Another possible metric trivially different from rms in this application is the standard deviation of the residual spectrum. Other metrics will require the residual spectrum to be first calculated.

In the present implementation the use of the rms value for each residual spectrum is the preferred form of metric. However other metrics might be used. For example the ratio of the peak to peak amplitude of a residue to its rms value will indicate possible structure in the residual. Further the number of runs in a residue indicates possible structure. Residual spectra typically have an average value close to zero. A run is a contiguous stretch of spectral data that all lies to the same side of zero. Data with structure tends to have fewer runs than random data. The sum of absolute area under each run can also show the presence of structure. The root mean square length of runs can also show the presence of structure. Thus these other metrics might be chosen in other implementations.

Up to this stage in the process no attempt has been made to see whether including adulterant spectra in the fit will lead to an improvement and hence an indication that the adulterant substance might be present in the sample. This is the next stage of the process.

In step 309 the principal factors from the PCA model are projected out of the adulterant spectra. Then in step 310 the adulterant residue data from step 309 is fitted to the sample residue data and validation residue data obtained in step 307. The result of this gives i) modified sample residue data which is residue data for the sample taking into account the effect of the adulterant spectra; and ii) modified validation residue data which is residue data for each validation example taking into account the adulterant spectra.

The resulting modified sample residue data and modified validation residue data resulting from this process is essentially equivalent to that which would be derived if the adulterant spectra were included in the PCA model. However it is computationally more efficient to separately project the principal factors out of the adulterant spectra in 309 and then perform a least-squares fit between the adulterant residue data and the sample residue data and validation residue data respectively.

Note that there may be a relatively large number of adulterant substances (and spectra) to be considered and also a relatively large number of validation examples to be considered. Further in the present techniques combinations of adulterant substances are considered and thus combinations of the adulterant residue data must also be considered in the fitting process of step 310. Thus there can be considerable processing required in carrying out step 310. Any trials with a negative fit coefficient in step 310 are rejected since adulterants are added to materials, not subtracted. Further, any trial with a fit coefficient less than the user selected threshold may also be rejected.

In step 311 statistical metrics of the modified residual spectra may be developed. Here the same metrics will be used as discussed above in relation to step 308. However what is being done at this stage is to determine those metrics for the modified sample residue data and modified validation residue data where the effect of including the adulterant spectra has been taken into account. Thus at this stage we have sample residue data, validation residue data for each validation example, modified sample residue data (taking the effect of adulterant spectra into account) and modified validation residue data (taking the effect of adulterant spectra into account) for each validation example.

In step 312 the metrics of each of these four types of residue data may be compared in order to help determine whether the relevant adulterant substance is present in the sample. In particular we want to determine if the improvement in the fit (reduction in the size of the residue) found by including the adulterants in the fit is significant. How does it compare to a random result? How does it compare to the results for the validation examples?

Thus as one example comparison which may be carried out, the difference in value between the metric for the sample residue data and the modified sample residue data may be compared to the corresponding difference between the modified validation residue data and the validation residue data. In particular the average difference in the validation residue data may be calculated and the standard deviation in the difference of the validation residue data may be calculated and the difference in sample residue data may be compared with this average plus three times the standard deviation. If the change in metric for the sample residue data is greater than the average plus three standard deviations for the validation residue data this signals the likely presence of the adulterant(s) concerned.

In step 313 the likelihood of an adulterant under consideration being present in the sample can be ranked. For each difference in metric three scores may be identified:

2 if the metric exceeds average+3 standard deviations
1 if the metric exceeds the maximum validation value observed
0 otherwise Such scores can be combined to give a rank in terms of likelihood. These might be given labels such as detected, likely, possible, unlikely and not detected.

In step 314 additional statistics may be computed and reported. Thus, for example, the significance of the change in any metric may be indicated. This may be calculated on the basis of the change in the metric between the sample residue data and the modified sample residue data compared with six times the standard deviation in the validation residue data across the whole set of validation examples.

Further the presence of unknown adulterants may be indicated. If the value of the metric for the sample residue data and for the modified sample residue data exceeds the average plus 3 standard deviations of the metric for the validation residue data across the whole validation set then it is likely that unknown adulterants are present in the sample and this may be indicated.

In step 315 results may be reported to the user concerning identified adulterants. This may be subject to a user determined minimum in adulterant concentration and/or adulterant likelihood that should be considered.

For any and all adulterant substances which exceed any such set limits the following may be reported—the adulterants—the determined likelihood—the estimated concentration of each adulterant—the estimated concentration detection limit—the value of the metric for the modified sample residual data.

In step 316 various spectra may be computed and output for inspection. All spectra will be presented filtered but unweighted. The spectra output may include the sample spectrum, the residual sample spectrum ignoring adulterants i.e. the sample residue data, the (combined) adulterant spectrum if any reported, the residual sample spectrum with adulterants fitted i.e. the modified sample residue data.

In step 317 a report may be given of the adulterant which best fits with the data i.e. that giving the lowest value of the metric for the modified sample residue data together with the estimated likelihood of this adulterant being actually present. This might be output where there are various adulterants that could fit or in circumstances where there is no adulterant that passes the user's minimum threshold setting. In step 317 there may also be a report on the possible presence of unknown adulterants where the sample data does not compare well with the validation data but none of the known adulterant spectra lead to a positive determination of the presence of one of those adulterants.

In a development of the process described above in relation to FIG. 3, then as well as comparing fitting of the adulterant spectra to both the sample data and validation data, consideration is also given to the effect of fitting the adulterant spectra to a randomised sample spectrum.

This is because when testing the reduction in sample residual spectrum metric as the adulterant fitting is introduced, it is helpful to know if the effect is significant when compared to a random result. One way of testing this is to fit the adulterants to a series of quasi-random sample residual spectra. Unfortunately sample residual spectra rarely appear to be random even when all reasonable spectral factors are accounted for. What is needed is a spectrum which has a rather similar distribution of features and resolutions but is otherwise random.

Thus in the present techniques such spectra may be created.

The method used to create such spectra is to take the sample residue spectra calculated in step 307 and appropriately process this. This sample residue spectra is operated upon to compute the discrete wavelet transform of the sample residue spectrum. At least of part of the resulting transform is multiplied point by point by a normally distributed sequence of random numbers with unit standard deviation. The very low frequency part of the transform may be left alone (ie not multiplied by random numbers) so that very slowly changing effects in the spectrum remain unaffected. The inverse transform is then performed on the result to give back a somewhat similar looking spectrum but differing randomly in its detail.

This may be repeated with different sequences of random numbers.

Once multiple such randomised sample residue spectra have been generated they may be used in a similar way as the validation residue data. Thus metrics may be calculated for the randomised sample residue data and the randomised sample residue data may be subjected to a least-square fit with the adulterant residue data to give modified randomised sample residue data. Once such additional residue data exists it may be used in comparing the effect of including effect of the adulterants. In particular a comparison may be made between the improvement in fit in the actual sample data found by taking the adulterant into account compared with the improvement in fit which occurs for the randomised data.

Clearly if the improvement in fit in the randomised data is equal or greater to that which is found for the real data then any effect for the real data can be ignored. Sometimes there may be a relatively low number of validation/calibration examples available for producing the calibration set of spectra and validation set of spectra. In such cases a number of different possibilities are available.

One way is to produce synthesised quasi-random residual spectra from one or more genuine residual spectra using the same method as just described above. Thus in such a case a residual spectra for one of the validation examples would be taken and a quasi-random synthesised residual spectra generated by performing a discrete wavelet transform on the initial residual spectrum, multiplying at least part of the transform point by point by a normally distributed sequence of random numbers with unit standard deviation, and then performing the inverse transform.

Another possibility is to accept that there are relatively low numbers of validation data and increase the number of standard deviations which are taken into account when performing comparisons. Thus rather than the average plus three standard deviations mentioned above, one might choose to use average+n standard deviations where n is larger than 3 and a function of a number of validation examples which are available. Thus n might be chosen to be 4 or 5 say.

An alternative is to use cross validation, for example "leave one out". In such a case, leaving one comparison spectrum out, a model is built from the remaining spectra and the residual spectrum of the one left out is calculated. Repeating this process for each comparison spectrum results in as many validation residual spectra as there are comparison spectra, at the expense of creating as many models. The model used for the sample spectrum residual is the full model built from all of the comparison spectrum. Note that it is also possible to leave more than one spectrum out at a time.

Further the step of generating a quasi-random spectrum may be achieved by picking the validation example with the greatest residue after projecting out of the principal factors and subjecting this validation example spectrum to a discrete wavelet transform, multiplying the result of the transform point by point by a normally distributed sequence of random numbers with unit standard deviation and then performing the inverse transform to get back to a somewhat similar looking spectrum. This resulting spectrum can then be used as an additional validation spectrum and subjected to the same process of projecting out principal factors and so on.

It will be recognised that within the processes described above a variety of different comparisons may actually be made and a variety of different metrics may be used in the decision making process of determining whether a particular adulterant is present in the sample. Further as will be clear from above, a particularly important part of any such decision making process is comparing the effect for the sample data and the validation data of including a consideration of the adulterant spectra.

In the applicant's currently preferred scoring system, rms of the residual spectra is chosen as the metric. As mentioned above, this has the advantage that the rms value of the residual spectra comes naturally out of the fitting processes performed and thus this metric can be used without first having to calculate the residual spectrum itself. This can help with processing. Standard deviation could be used instead. At a later stage the residual spectrum of interest can be calculated where this is useful for other purposes or for example for reporting to the user. However it can be particularly advantageous not to have to calculate the residual spectra in all cases for all of the comparisons which are being made in the process of determining which adulterant and combinations of adulterants might be present.

The applicant's currently preferred scoring system is as follows. This is a system for scoring the likelihood of a specific adulterant mixture being present and involves the use of the following metrics:

a) the rms of the sample residual spectrum, including adulterant i.e. modified sample residue data
b) the rms of the sample residual spectrum, excluding adulterant i.e. sample residue data
c) the difference of a) and b)
d) the estimated concentration of each mixture adulterant in the sample
e) the rms of each validation residual spectrum, including adulterant i.e. modified validation residue data, for each validation example
f) the rms of each validation residual spectrum, excluding adulterant i.e. validation residue data, for each validation example
g) the difference of e) and f) for each validation example
h) the estimated concentration of each mixture adulterant in each validation sample
i) the rms difference of each quasi-random synthesized sample residual spectrum, excluding versus including adulterant i.e. rms (randomised sample residue data)— rms (modified randomised sample residue data) for each quasi-random spectrum Measures e) through h) apply to multiple validation spectra and therefore have an average value, a maximum observed value and a standard deviation a leading to a limit value of average+3$\sigma$ (limit>max). Similarly, measure i)

applies to multiple quasi-random sample residual spectra and so have an average, max and limit calculated on the same basis. With these metrics, the currently employed likelihood scoring algorithm is:

| If | a) < max e) | and |
| | b) > limit f) | and |
| | c) > limit g) | and |
| | c) > limit i) | and |
| | d) > limit h) | for all adulterant mixture components |
| then | likelihood is detected | |
| else if | c) > limit g) | and |
| | c) > limit i) | and |
| | d) > limit h) | for all adulterant mixture components |
| then | likelihood is likely | |
| else if | a) >= max e) | |
| then | likelihood is possible | |
| else if | a) < max e) | and |
| | b) < max f) | and |
| | c) < max g) | and |
| | c) < max i) | and |
| | d) < max h) | for all adulterant mixture components |
| then | likelihood is not detected | |
| else | likelihood is not likely | |

Such scoring is repeated for each adulterant in the library and each allowed adulterant combination (currently limited to combinations of up to 3 adulterants).

This scoring methodology could be used with a different metric, perhaps most clearly using standard deviation in place of rms, but also other metrics.

Of course a different scoring methodology could be used and for example the limit value might be determined using a number of standard deviations other than 3 if desired.

The invention claimed is:

1. A method for identifying the presence of at least one adulterant substance in a physical sample in connection with a spectrometer, the method comprising:
   receiving, by an analysis module of a spectrometer, a set of sample spectral data acquired for a sample, via the spectrometer;
   receiving, by the analysis module, a set of reference spectral data;
   receiving, by the analysis module, a plurality of sets of validation spectral data, each set for a respective validation example;
   receiving, by the analysis module, a set of adulterant substance spectral data for said at least one adulterant substance;
   determining, by a spectral data processor executing on the analysis module, sample residue data which is representative of a residue which would remain after performing a least squares fitting process between the sample spectral data and the reference spectral data;
   determining, by the spectral data processor, modified sample residue data which is representative of a residue which would remain after performing a least squares fitting process between the sample spectral data, the reference spectral data and the adulterant substance spectral data;
   for each validation example, determining, by the spectral data processor, validation residue data which is representative of a residue which would remain after performing a least squares fitting process between the validation spectral data for the respective example and the reference spectral data;
   for each validation example, determining, by the spectral data processor, modified validation residue data which is representative of a residue which would remain after performing a least squares fitting process between the validation spectral data for the respective example, the reference spectral data and the adulterant substance spectral data;
   performing, by the spectral data processor, at least one comparison amongst the sample residue data, the modified sample residue data, the validation residue data, and the modified validation residue data;
   determining, by the spectral data processor, a likelihood value for the presence of said at least one adulterant substance in said sample in dependence on said at least one comparison; and
   generating, by the analysis module using the likelihood value, a label for the adulterant substance indicating a likelihood that the adulterant substance is present in the physical sample.

2. The method according to claim 1, wherein the performing of the at least one comparison, by the spectral data processor, comprises,
   a) determining, by the spectral data processor, a value of a metric in respect of:
      i) the sample residue data;
      ii) the modified sample residue data;
      iii) the validation residue data for each validation example; and
      iv) the modified validation residue data for each validation example.

3. The method according to claim 2, wherein the rms of a respective residual spectrum is chosen as the metric.

4. The method according to claim 1, wherein the performing of the at least one comparison, by the spectral data processor, comprises,
   a) determining, by the spectral data processor, a value of a metric in respect of:
      i) the sample residue data;
      ii) the modified sample residue data;
      iii) the validation residue data for each validation example; and
      iv) the modified validation residue data for each validation example,
   b) determining, by the spectral data processor, a maximum value of the metric for:
      i) the validation residue data across the validation examples; and
      ii) the modified validation residue data across the validation examples,
   c) determining, by the spectral data processor, an average value of the metric for:
      i) the validation residue data across the validation examples; and
      ii) the modified validation residue data across the validation examples, and
   d) determining, by the spectral data processor, a standard deviation value of the metric for:
      i) the validation residue data across the validation examples; and
      ii) the modified validation residue data across the validation examples.

5. The method according to claim 1, wherein the performing of the at least one comparison, by the spectral data processor, comprises,
   a) determining, by the spectral data processor, a value of a metric in respect of:
      i) the sample residue data;
      ii) the modified sample residue data;
      iii) the validation residue data for each validation example; and iv) the modified validation residue data for each validation example,
b) determining, by the spectral data processor, a maximum value of the metric for:
  i) the validation residue data across the validation examples; and
  ii) the modified validation residue data across the validation examples, and
c) performing at least one comparison, by the spectral data processor, between the value of the metric for at least one of the sample residue data and the modified sample residue on the one hand and the determined maximum value of the metric for at least one of the validation residue data and the modified validation residue data on the other hand.

6. The method according to claim 1, wherein the performing of the at least one comparison, by the spectral data processor, comprises,
  a) determining, by the spectral data processor, a value of a metric in respect of:
    i) the sample residue data;
    ii) the modified sample residue data;
    iii) the validation residue data for each validation example;
    iv) the modified validation residue data for each validation example,
  b) determining, by the spectral data processor, an average value of the metric for:
    i) the validation residue data across the validation examples;
    ii) the modified validation residue data across the validation examples,
  c) determining, by the spectral data processor, a standard deviation value of the metric for:
    i) the validation residue data across the validation examples;
    ii) the modified validation residue data across the validation examples,
  and
  d) performing at least one comparison, by the spectral data processor, between,
    the value of the metric for at least one of the sample residue data and the modified sample residue on the one hand, and
    at least one of:
    i) the average for the validation residue data determined in b) plus a predetermined number (n) times the standard deviation for the validation residue data calculated in c); and
    ii) the average for the modified validation residue data determined in b) plus a predetermined number (n) times the standard deviation for the modified validation residue data calculated in c)
    on the other hand.

7. The method according to claim 1, wherein the performing of the at least one comparison, by the spectral data processor, comprises,
  a) determining, by the spectral data processor, a value of a metric in respect of:
    i) the sample residue data;
    ii) the modified sample residue data;
    iii) the validation residue data for each validation example; and
    iv) the modified validation residue data for each validation example,
  b) calculating, by the spectral data processor, the difference between the value of the metric for the sample residue data and the value of the metric for the modified sample residue data,
  c) for each validation example, calculating, by the spectral data processor, the difference between the value of the metric for the validation residue data and the value of the metric for the modified validation residue data,
  d) determining, by the spectral data processor, an average difference between the value of the metric for the validation residue data and the value of the metric for the modified validation residue data across the validation examples,
  e) determining, by the spectral data processor, a standard deviation in the difference between the value of the metric for the validation residue data and the value of the metric for the modified validation residue data across the validation examples,
  f) comparing, by the spectral data processor, the difference between the value of the metric for the sample residue data and the value of metric for the modified sample residue data calculated in c) to the average determined in d) plus a predetermined number (n) times the standard deviation calculated in e).

8. The method according to claim 1, further comprising generating, by the analysis module, an indicator that the sample likely includes an adulterant which is distinct from said at least one adulterant in response to a determination, by the spectral data processor, that
  i) the determined value of a metric in respect of the sample residue data is greater than the average for the validation residue data plus 3 times the standard deviation for the validation residue data; and
  ii) the determined value of a metric in respect of the modified sample residue data is greater than the average for the modified validation residue data determined in plus 3 times the standard deviation for the modified validation residue data.

9. The method according to claim 1, further comprising:
  receiving, by the analysis module, a set of adulterant substance spectral data for a plurality of adulterant substances,
  determining, by the spectral data processor, respective modified sample residue data which is representative of a residue which would remain after performing a least squares fitting process between the sample spectral data, the reference spectral data and each set of adulterant substance spectral data, and
  for each validation example, determining, by the spectral data processor, respective modified validation residue data which is representative of a residue which would remain after performing a least squares fitting process between the validation spectral data for the respective example, the reference spectral data and each set of adulterant substance spectral data, wherein
  the performing of the at least one comparison, by the spectral data processor, comprises performing, by the spectral data processor, at least one comparison in respect of each adulterant substance;
  determining, by the spectral data processor, a likelihood value for the presence of each adulterant substance in said sample in dependence on said at least one comparison; and
  generating, by the analysis module using the likelihood value for the presence of each adulterant, a label for each respective adulterant substance indicating a likelihood that the respective adulterant substance is present in the physical sample.

10. The method according to claim 1, further comprising:

receiving, by the analysis module, a set of adulterant substance spectral data for a plurality of adulterant substance, determining, by the spectral data processor, respective modified sample residue data which is representative of a residue which would remain after performing a least squares fitting process between the sample spectral data, the reference spectral data and at least one selected combination of sets of adulterant substance spectral data, and for each validation example, determining, by the spectral data processor, respective modified validation residue data which is representative of a residue which would remain after performing a least squares fitting process between the validation spectral data for the respective example, the reference spectral data and the at least one selected combination of sets of adulterant substance spectral data, wherein the performing of the at least one comparison, by the spectral data processor, comprises performing, by the spectral data processor, at least one comparison in respect of each selected combination of adulterant substances;

determining, by the spectral data processor, a likelihood value for the presence of each selected combination of adulterant substances in said sample in dependence on said at least one comparison; and generating, by the analysis module using the likelihood value for the presence of each adulterant, a label for each respective adulterant substance indicating a likelihood that the respective adulterant substance is present in the physical sample.

11. The method according to claim 1, wherein the validation residue data comprises a residual spectrum, and further comprising creating, by the spectral data processor, an additional validation residue spectrum by at least:

computing, by the spectral data processor, a discrete wavelet transform of the validation residue spectrum for one validation example;

multiplying, by the spectral data processor, at least part of the transform point by point by a normally distributed sequence of random numbers with unit standard deviation to provide a modified transform; and performing, by the spectral data processor, an inverse of the discrete wavelet transform on the modified transform to produce a spectrum which is usable as an additional validation residue spectrum.

12. The method according to claim 1, wherein the sample residue data comprises a residual spectrum, and further comprising generating, by the spectral data processor, at least one randomly altered sample residue spectrum by at least:

computing, by the spectral data processor, a discrete wavelet transform of the sample residue data;

multiplying, by the spectral data processor, at least part of the transform point by point by a normally distributed sequence of random numbers with unit standard deviation to provide a modified transform; and performing, by the spectral data processor, an inverse of the discrete wavelet transform operation on the modified transform to produce a spectrum which is usable as a randomly altered sample residue spectrum.

13. The method according to claim 12, further comprising determining, by the spectral data processor, modified randomly altered sample residue data which is representative of a residue which would remain after performing a least squares fitting process between the respective randomized spectrum, the reference spectral data and the adulterant substance spectral data.

14. The method according to claim 13, wherein the performing of the at least one comparison, by the spectral data processor, comprises performing, by the spectral data processor, at least one comparison amongst the sample residue data, the modified sample residue data, the validation residue data, the modified validation residue data, randomly altered sample residue data, and modified randomly altered sample residue data, and also where present, the additional validation residue data, and the modified additional validation residue data.

15. The method according to claim 14, wherein the performing of the at least one comparison, by the spectral data processor, comprises:

a) for each randomized spectrum, calculating, by the spectral data processor, the difference between the value of the metric for the randomly altered sample residue data and the value of the metric for the modified randomly altered sample residue data, and at least one of:

b) determining, by the spectral data processor, an average difference between the value of the metric for the randomly altered sample residue data and the value of the metric for the modified randomly altered sample residue data across the data set, c) determining, by the spectral data processor, a standard deviation in the difference between the value of the metric for the randomly altered sample residue data and the value of the metric for the modified randomly altered sample residue data across the data set, and d) determining, by the spectral data processor, a maximum difference between the value of the metric for the randomly altered sample residue data and the value of the metric for the modified randomly altered sample residue data across the data set.

16. The method according to claim 15, wherein the performing of the at least one comparison, by the spectral data processor, comprises, a) determining, by the spectral data processor, a value of a metric in respect of:
  i) the sample residue data;
  ii) the modified sample residue data;
  iii) the randomly altered sample residue data for each randomized spectrum; and
  iv) the modified randomly altered sample residue data for each randomized spectrum;

b) calculating, by the spectral data processor, the difference between the value of the metric for the sample residue data and the value of metric for the modified sample residue data, c) for each randomized spectrum, calculating, by the spectral data processor, the difference between the value of the metric for the randomly altered sample residue data and the value of the metric for the modified randomly altered sample residue data, d) determining, by the spectral data processor, an average difference between the value of the metric for the randomly altered sample residue data and the value of the metric for the modified randomly altered sample residue data across the data set, e) determining, by the spectral data processor, a standard deviation in the difference between the value of the metric for the randomly altered sample residue data and the value of the metric for the modified randomly altered sample residue data across the data set, and f) comparing, by the spectral data processor, the difference between the value of the metric for the sample residue data and the value of metric for the modified sample residue data calculated in c) to the average determined in d) plus a predetermined number (n) times the standard deviation calculated in e).

17. The method according to claim 15 wherein the performing of the at least one comparison, by the spectral data processor, comprises, a) determining, by the spectral data processor, a value of a metric in respect of:
   i) the sample residue data;
   ii) the modified sample residue data;
   iii) the randomly altered sample residue data for each randomized spectrum; and
   iv) the modified randomly altered sample residue data for each randomized spectrum;

b) calculating, by the spectral data processor, the difference between the value of the metric for the sample residue data and the value of metric for the modified sample residue data, c) for each randomized spectrum, calculating, by the spectral data processor, the difference between the value of the metric for the randomly altered sample residue data and the value of the metric for the modified randomly altered sample residue data, d) determining, by the spectral data processor, a maximum difference between the value of the metric for the randomly altered sample residue data and the value of the metric for the modified randomly altered sample residue data across the data set, and e) comparing, by the spectral data processor, the difference between the value of the metric for the sample residue data and the value of metric for the modified sample residue data calculated in c) to the maximum difference determined in d).

18. The method according to claim 1, wherein the determining of sample residue data, the determining of modified sample residue data, the determining of validation residue data, and the determining of modified validation residue data are carried out by directly performing, by the spectral data processor, the respective least squares fitting processes.

19. The method according to claim 1, further comprising:
developing a principal components analysis model of a calibration set of data to produce a set of principal factors which represent the set of reference spectral data;
projecting, by the spectral data processor, the principal factors out of the sample spectral data to leave the sample residue data;
projecting, by the spectral data processor, the principal factors out of the validation spectral data, each set for a respective validation example to leave the validation residue data;
projecting, by the spectral data processor, the principal factors out of the adulterant substance spectral data for said at least one adulterant substance to leave adulterant residue data;
least squares fitting, by the spectral data processor, the sample residue data with the adulterant residue data to generate the modified sample residue data; and least squares fitting, by the spectral data processor, the validation residue data with the adulterant residue data to generate the modified validation residue data.

20. The method according to claim 19, further comprising having a plurality of sets of spectral data for different adulterant substances, and wherein combinations of the adulterant residue data for the respective substances are used in the least squares fitting processes, by the spectral data processor, to generate the appropriate modified sample residue data and modified validation residue data.

21. A method for identifying the presence of at least one adulterant substance in a physical sample, the method comprising:
receiving, by an analysis module of a spectrometer, a set of sample spectral data acquired for a sample;
receiving, by the analysis module, a plurality of sets of calibration spectral data for use in generating a set of reference spectral data, each set of calibration spectral data being for a respective calibration example;
receiving, by the analysis module, a plurality of sets of validation spectral data, each set for a respective validation example;
receiving, by the analysis module, a set of adulterant substance spectral data for said at least one adulterant substance;
developing a principal components analysis model of the calibration sets of data to produce a set of principal factors which represent the set of reference spectral data;
projecting, by a spectral data processor executing on the analysis module, the principal factors out of the sample spectral data to leave sample residue data;
projecting, by the spectral data processor, the principal factors out of each set of validation spectral data to leave validation residue data for each validation example;
projecting, by the spectral data processor, the principal factors out of the adulterant substance spectral data for said at least one adulterant substance to leave adulterant residue data;
least squares fitting, by the spectral data processor, the sample residue data with the adulterant residue data to generate modified sample residue data, which represents an effect of taking the adulterant spectral data into account in the principal components analysis model;
least squares fitting, by the spectral data processor, the validation residue data with the adulterant residue data to generate the modified validation residue data, which represents an effect of taking the adulterant spectral data into account in the principal components analysis model,
performing, by the spectral data processor, at least one comparison amongst the sample residue data, the modified sample residue data, the validation residue data, and the modified validation residue data;
determining, by the spectral data processor, a likelihood value for the presence of said at least one adulterant substance in said sample in dependence on said at least one comparison; and
generating, by the analysis module using the likelihood value, a label for the adulterant substance indicating a likelihood that the adulterant substance is present in the physical sample said likelihood value.

22. A spectrometer arranged for identifying the presence of at least one adulterant substance in a physical sample, the spectrometer comprising:

a hardware processor programmed to control the spectrometer to at least:

acquire a set of sample spectral data for a physical sample at an analysis module of the spectrometer;

determine or receive, at the analysis module, a set of reference spectral data, acquire or receive, at the analysis module, a plurality of sets of validation spectral data, each set for a respective validation example;

acquire or receive, at the analysis module, a set of adulterant substance spectral data for said at least one adulterant substance;

determine, by a spectral data processor executing on the analysis module, sample residue data which is representative of a residue which would remain after performing a least squares fitting process between the sample spectral data and the reference spectral data;

determine, by the spectral data processor, modified sample residue data which is representative of a residue which would remain after performing a least squares fitting process between the sample spectral data, the reference spectral data and the adulterant substance spectral data;

for each validation example, determine, by the spectral data processor, validation residue data which is representative of a residue which would remain after performing a least squares fitting process between the validation spectral data for the respective example and the reference spectral data;

for each validation example, determine, by the spectral data processor, modified validation residue data which is representative of a residue which would remain after performing a least squares fitting process between the validation spectral data for the respective example, the reference spectral data and the adulterant substance spectral data;

perform, by the spectral data processor, at least one comparison amongst the sample residue data, the modified sample residue data, the validation residue data, and the modified validation residue data;

determine, by the spectral data processor, a likelihood value for the presence of said at least one adulterant substance in said sample in dependence on said at least one comparison; and generate, by the analysis module using the likelihood value, a label for the adulterant substance indicating a likelihood that the adulterant substance is present in the physical sample.

23. A computer arranged under the control of software for processing spectral data to identify the presence of at least one adulterant substance in aphysical sample, the computer comprising:

processing resources including a hardware processor and a memory operably coupled thereto, the memory storing the software, and the processing resources being configured to run the software to control the computer to at least:

receive, by the computer, a set of sample spectral data for a physical sample;

determine or receive, by the computer, a set of reference spectral data;

receive, by the computer, a plurality of sets of validation spectral data, each set for a respective validation example;

receive, by the computer, a set of adulterant substance spectral data for said at least one adulterant substance;

determine, by the computer, sample residue data which is representative of a residue which would remain after performing a least squares fitting process between the sample spectral data and the reference spectral data;

determine, by the computer, modified sample residue data which is representative of a residue which would remain after performing a least squares fitting process between the sample spectral data, the reference spectral data and the adulterant substance spectral data;

for each validation example, determine, by the computer, validation residue data which is representative of a residue which would remain after performing a least squares fitting process between the validation spectral data for the respective example and the reference spectral data;

for each validation example, determine, by the computer, modified validation residue data which is representative of a residue which would remain after performing a least squares fitting process between the validation spectral data for the respective example, the reference spectral data and the adulterant substance spectral data;

perform, by the computer, at least one comparison amongst the sample residue data, the modified sample residue data, the validation residue data, and the modified validation residue data;

determine, by the computer, a likelihood value for the presence of said at least one adulterant substance in said sample in dependence on said at least one comparison; and generate, by the computer using the likelihood value, a label for the adulterant substance indicating a likelihood that the adulterant substance is present in the physical sample.

24. A non-transitory computer readable storage medium tangibly storing a computer program for identifying the presence of at least one adulterant substance in a physical sample, the computer program comprising code portions which, when loaded and run on a computer, cause the computer to execute functionality comprising:

receiving, by the computer, a set of sample spectral data acquired for a physical sample;

receiving, by the computer, a set of reference spectral data;

receiving, by the computer, a plurality of sets of validation spectral data, each set for a respective validation example;

receiving, by the computer, a set of adulterant substance spectral data for said at least one adulterant substance;

determining, by the computer, sample residue data which is representative of a residue which would remain after performing a least squares fitting process between the sample spectral data and the reference spectral data;

determining, by the computer, modified sample residue data which is representative of a residue which would remain after performing a least squares fitting process between the sample spectral data, the reference spectral data and the adulterant substance spectral data;

for each validation example, determining, by the computer, validation residue data which is representative of a residue which would remain after performing a least squares fitting process between the validation spectral data for the respective example and the reference spectral data;

for each validation example, determining, by the computer, modified validation residue data which is representative of a residue which would remain after performing a least squares fitting process between the validation spectral data for the respective example, the reference spectral data and the adulterant substance spectral data;

performing, by the computer, at least one comparison amongst the sample residue data, the modified sample residue data, the validation residue data, and the modified validation residue data;

determining, by the computer, a likelihood value for the presence of said at least one adulterant substance in said sample in dependence on said at least one comparison; and generating, by the computer using the likelihood value, a label for the adulterant substance indicating a likelihood that the adulterant substance is present in the physical sample.

25. A non-transitory computer readable storage medium tangibly storing a computer program for identifying the presence of at least one adulterant substance in a physical sample, the computer program comprising code portions which, when loaded and run on a computer, cause the computer to execute functionality comprising:

receiving, by the computer, a set of sample spectral data acquired for a physical sample;

receiving, by the computer, a plurality of sets of calibration spectral data for use in generating a set of reference spectral data, each set of calibration spectral data being for a respective calibration example;

receiving, by the computer, a plurality of sets of validation spectral data, each set for a respective validation example;

receiving, by the computer, a set of adulterant substance spectral data for said at least one adulterant substance;

developing a principal components analysis model of the calibration sets of data to produce a set of principal factors which represent the set of reference spectral data;

projecting, by the computer, the principal factors out of the sample spectral data to leave sample residue data;

projecting, by the computer, the principal factors out of each set of validation spectral data to leave validation residue data for each validation example;

projecting, by the computer, the principal factors out of the adulterant substance spectral data for said at least one adulterant substance to leave adulterant residue data;

least squares fitting, by the computer, the sample residue data with the adulterant residue data to generate modified sample residue data, which represents an effect of taking the adulterant spectral data into account in the principal components analysis model;

least squares fitting, by the computer, the validation residue data with the adulterant residue data to generate the modified validation residue data, which represents an effect of taking the adulterant spectral data into account in the principal components analysis model, performing, by the computer, at least one comparison amongst the sample residue data, the modified sample residue data, the validation residue data, and the modified validation residue data;

determining, by the computer, a likelihood value for the presence of said at least one adulterant substance in said sample in dependence on said at least one comparison; and generating, by the computer using the likelihood value, a label for the adulterant substance indicating a likelihood that the adulterant substance is present in the physical sample.

26. A method for identifying the presence of at least one adulterant substance in a physical sample using a spectrometer, the method being non-invasive and non-destructive relative to the sample and lacking wet chemical analysis of the sample, the method comprising:

receiving, by an analysis module of the spectrometer, a set of sample spectral data acquired for the physical sample;

receiving, by the analysis module, a set of reference spectral data from physical objects;

receiving, by the analysis module, a plurality of sets of validation spectral data, each set for a respective validation example, wherein the sample spectral data and the validation spectral data are allowed to vary within one of a plurality of different definable classes of sample types;

receiving, by the analysis module, a set of adulterant substance spectral data for said at least one adulterant substance;

determining, by a spectral data processor executing on the analysis module, sample residue data which is representative of a residue which would remain after performing a least squares fitting process between the sample spectral data and the reference spectral data;

determining, by the spectral data processor, modified sample residue data which is representative of a residue which would remain after performing a least squares fitting process between the sample spectral data, the reference spectral data and the adulterant substance spectral data;

for each validation example, determining, by the spectral data processor, validation residue data which is representative of a residue which would remain after performing a least squares fitting process between the validation spectral data for the respective example and the reference spectral data;

for each validation example, determining, by the spectral data processor, modified validation residue data which is representative of a residue which would remain after performing a least squares fitting process between the validation spectral data for the respective example, the reference spectral data and the adulterant substance spectral data;

performing at least one comparison, by the spectral data processor, amongst the residue data, wherein the modified sample residue data, the validation residue data, and the modified validation residue data, the sample residue data, the modified sample residue data, the validation residue data, and the modified validation residue data are compatible with one another by virtue of having a common start and end wavenumber/wavelength and data interval;

identifying, by the spectral data processor, said at least one adulterant substance in said sample;

determining, by the spectral data processor, a likelihood value for the presence of said at least one adulterant substance in said sample in dependence on said at least one comparison; and generating, by the analysis module using the likelihood value, a label for the adulterant substance indicating a likelihood that the adulterant substance is present in the physical samples.

* * * * *